United States Patent [19]

Kocal et al.

[11] Patent Number: 5,169,812
[45] Date of Patent: Dec. 8, 1992

[54] CATALYST AND PROCESS FOR PRODUCING AROMATIC COMPOUNDS FROM $C_2$-$C_6$ ALIPHATIC HYDROCARBONS

[75] Inventors: Joseph A. Kocal, Gurnee; Tamotsu Imai, Mt. Prospect; Paul J. Kuchar, Hinsdale; Christopher D. Gosling, Roselle, all of Ill.

[73] Assignee: UOP, Des Plaines, Ill.

[21] Appl. No.: 760,294

[22] Filed: Sep. 16, 1991

[51] Int. Cl.$^5$ .............................. B01J 00/00
[52] U.S. Cl. .................................. 502/61; 502/71; 502/85; 502/86
[58] Field of Search .............. 502/61, 85, 86, 71

[56] References Cited

U.S. PATENT DOCUMENTS

| | | | |
|---|---|---|---|
| 3,725,249 | 4/1973 | Vesely et al. | 208/139 |
| 4,594,333 | 6/1986 | Chang et al. | 502/85 |
| 4,596,704 | 6/1986 | Miale et al. | 502/86 |
| 4,629,717 | 12/1986 | Chao | 502/208 |
| 4,654,455 | 3/1987 | Chao | 585/415 |
| 4,746,763 | 5/1988 | Kocal | 585/417 |
| 5,081,084 | 1/1992 | Sachtler et al. | 502/61 |

Primary Examiner—Carl F. Dees
Attorney, Agent, or Firm—Thomas K. McBride; Eugene I. Snyder; Frank S. Molinaro

[57] ABSTRACT

A catalyst for converting $C_2$ to $C_6$ aliphatic hydrocarbons to aromatics is described. The catalyst contains a zeolite, an aluminum phosphate binder and a gallium component. Examples of zeolites which can be used are the ZSM family of zeolites, with ZSM-5 being a specific example. The catalyst is characterized in that it is tolerant to exposure to hydrogen at tempertures of about 500° to about 700° C. The catalyst's tolerance to hydrogen exposure is the result of treating the catalyst with an aqueous solution of a weakly acidic ammonium salt or a dilute acid solution at a temperature of about 50° to about 100° C. for a time of about 1 to about 48 hours, followed by calcination. A process for preparing the catalyst is also described.

9 Claims, No Drawings

CATALYST AND PROCESS FOR PRODUCING AROMATIC COMPOUNDS FROM $C_2$-$C_6$ ALIPHATIC HYDROCARBONS

FIELD OF THE INVENTION

The present invention relates to a catalyst and to a process using the catalyst for the production of aromatic hydrocarbons via the dehydrocyclodimerization of $C_2$-$C_6$ aliphatic hydrocarbons. The catalyst is characterized in that it is tolerant to exposure to hydrogen at a temperature of about 500° to about 700° C.

BACKGROUND OF THE INVENTION

Dehydrocyclodimerization is a process in which aliphatic hydrocarbons containing from 2 to 6 carbon atoms per molecule are reacted over a catalyst to produce a high yield of aromatics and hydrogen, with a light ends byproduct, $C_2$-$C_4$ recycle product and a trace $C_4^+$ nonaromatic byproduct. This process is well known and is described in detail in U.S. Pat. Nos. 4,654,455 and 4,746,763 which are incorporated by reference. Typically, the dehydrocyclodimerization reaction is carried out at temperatures in excess of 500° C., using dual functional catalysts containing acidic and dehydrogenation components. The acidic function is usually provided by a zeolite which promotes the oligomerization and aromatization reactions, while a non-noble metal component promotes the dehydrogenation function. One specific example of a catalyst disclosed in U.S. Pat. No. 4,746,763 consists of a ZSM-5 type zeolite, gallium and a phosphorus containing alumina as a binder.

The conditions used for the dehydrocyclodimerization reaction result in rapid catalyst deactivation which is believed to be caused by excessive carbon formation (coking) on the catalyst surface. This coking tendency makes it necessary to frequently perform catalyst regenerations. In addition, applicants have noted that the prior art catalyst can be deactivated by exposure to hydrogen at temperatures greater than 500° C. Minimizing the deactivation caused by this hydrogen exposure is a particular object of this invention.

Applicants' catalyst contains a zeolite, a gallium component and an aluminum phosphate binder, but is characterized in that it is tolerant to hydrogen exposure at temperatures greater than 500° C. The ability of the catalyst of this invention to withstand extended exposure to hydrogen without significant loss of activity is achieved by treating the catalyst with an aqueous solution of a weakly acidic ammonium salt or a dilute acid solution. This treatment removes some aluminum and phosphorus (and small amounts of silicon) from the catalyst as evidenced by analysis of the wash water. It is believed that this treatment removes an aluminum/phosphorus species which has deleterious effects on the catalyst when exposed to hydrogen at high temperatures. Since the catalyst is exposed to such conditions during normal operation, the ability to remove such a deleterious species results in the unexpected result of increased catalyst life.

SUMMARY OF THE INVENTION

As stated, the instant invention relates to a catalyst, a process for preparing the catalyst and a process for using the catalyst. Thus, one embodiment of the invention is a catalyst for converting $C_2$ to $C_6$ aliphatic hydrocarbons to aromatics comprising a zeolite having a Si:Al ratio greater than about 10 and a pore diameter of about 5-6 Å, a gallium component and an aluminum phosphate binder, the catalyst characterized in that it is tolerant to exposure to hydrogen at a temperature of about 500° to about 700° C.

Another embodiment of the invention is a process for preparing a catalyst for converting $C_2$ to $C_6$ aliphatic hydrocarbons to aromatics comprising: a) forming particles from a mixture of a zeolite and an aluminum phosphate binder; b) calcining said particles at a temperature of about 500° to about 700° C. and for a time of about 1 to about 15 hours; c) impregnating the calcined particles with a gallium salt; d) heating the gallium containing particles in hydrogen at a temperature of about 500° to about 700° C. for a time of about 1 to about 15 hours, followed by heating in an air/steam mixture at a temperature of about 400° to about 700° C. for a time of about 1 to about 10 hours; e) treating the particles of step (d) with an aqueous solution of a weakly acidic ammonium salt or a dilute acid solution at a temperature of about 50° to about 100° C. for a time of about 1 to about 48 hours; and f) calcining the particles at a temperature of about 500° to about 700° C. for a time of about 1 to about 15 hours, thereby providing said catalyst.

Yet another embodiment of the invention is a process for converting $C_2$ to $C_6$ aliphatic hydrocarbons to aromatic compounds comprising contacting a feed stream containing $C_2$ to $C_6$ aliphatic hydrocarbons with a catalyst at dehydrocyclodimerization conditions to provide aromatic compounds, the catalyst comprising a zeolite having a Si:Al ratio greater than about 10 and a pore diameter of about 5-6 Å, a gallium component and an aluminum phosphate binder, the catalyst characterized in that it is tolerant to exposure to hydrogen at a temperature of about 500° to about 700° C.

DETAILED DESCRIPTION OF THE INVENTION

As stated, this invention relates to a catalyst, a process for preparing the catalyst and a process for using the catalyst. The catalyst of the present invention comprises a zeolite component, a binder component, and a gallium metal component. The zeolites which may be used are any of those which have a Si:Al ratio greater than about 10 and preferably greater than 20 and a pore diameter of about 5 to 6 Angstroms. Specific examples of zeolites which can be used are the ZSM family of zeolites. Included among this ZSM family are ZSM-5, ZSM-8, ZSM-11, ZSM-12 and ZSM-35.

The preparation of these ZSM-type zeolites is well known in the art and generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to about 90 weight percent and preferably from about 50 to about 70 weight percent of the catalyst.

A second component of the catalyst of this invention is a phosphorus containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well-known oil drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to about 1.5:1 weight ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis.

The resulting aluminum phosphate hydrosol mixture is now gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 93° C. to about 149° C. (200°–300° F.) and subjected to a calcination procedure at a temperature of about 450° C. to about 703° C. (850°–1300° F.) for a period of about 1 to about 20 hours. The amount of phosphorus containing alumina component present (as the oxide) in the catalyst can range from about 10 to about 70 weight percent and preferably from about 30 to about 50 weight percent.

The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are calcined as described above to give a support.

Another necessary component of the instant catalyst is a gallium component. The gallium component may be deposited onto the support in any suitable manner known to the art which results in a uniform dispersion of the gallium. Usually the gallium is deposited onto the support by impregnating the support with a salt of the gallium metal. The particles are impregnated with a gallium salt selected from the group consisting of gallium nitrate, gallium chloride, gallium bromide, gallium hydroxide, gallium acetate, etc. The amount of gallium which is deposited onto the support varies from about 0.1 to about 5 weight percent of the finished catalyst expressed as the metal.

The gallium compound may be impregnated onto the support particles by any technique well known in the art such as dipping the catalyst into a solution of the metal compound or spraying the solution onto the support. One preferred method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket. After the particles are completely dry, they are heated under a hydrogen atmosphere at a temperature of about 500° to about 700° C. for a time of about 1 to about 15 hours. Although a pure hydrogen atmosphere is preferred to reduce and disperse the gallium, the hydrogen may be diluted with nitrogen. Alternatively, it is envisioned that the reduction and dispersion can be done in situ in the actual reactor vessel used for dehydrocyclodimerization by using either pure hydrogen or a mixture of hydrogen and hydrocarbons. Next the hydrogen treated particles are heated in air and steam at a temperature of about 400° to about 700° C. for a time of about 1 to about 10 hours. The amount of steam present in the air varies from about 1 to about 40 percent.

These catalyst particles which now contain well dispersed gallium present as gallium oxide are treated with an aqueous solution of a weakly acidic ammonium salt or a dilute acid solution. The ammonium salts which can be used include ammonium chloride, ammonium acetate and ammonium nitrate. The concentration of these salts can vary from about 0.1 to about 5 molar. The acids which can be used include hydrochloric, acetic, nitric and sulfuric acid. Although concentrated acids could be used, they would degrade the zeolite and the integrity of the particles as well as removing the undesirable aluminum phosphorus species. Thus, it is desirable to use dilute acids which have a molarity from about 0.1 to about 5 moles/liter. Of these treatment solutions, it is preferred to use an ammonium nitrate solution.

The treating solution is contacted with the calcined catalyst particles at a temperature of about 50° to about 100° C. for a time of about 1 to about 48 hours. After this treatment, the particles are separated from the aqueous solution, dried and calcined at a temperature of about 500° to about 700° C. for a time of about 1 to about 15 hours, thereby providing the catalyst of the instant invention.

The purpose of treating the support with one of the solutions described above is to remove materials which cause the catalyst to deactivate when it is exposed to hydrogen (hydrogen is produced during the dehydrocyclodimerization process) at temperatures above 500° C. and specifically temperatures between 500° and 700° C. The exact nature of the species which is removed by this treatment step is not known. Without wishing to be bound by a particular theory, it is postulated that the deleterious species which is removed is an aluminum/phosphorus species. This hypothesis is based on the analysis of the wash water after the catalyst has been treated. The wash water also contains small amounts of silicon indicating that the deleterious species may also contain silicon.

Although the exact nature of the species which is removed is not known, it is observed that treating a catalyst which contains an aluminum phosphate binder with one of the solutions described above renders the catalyst tolerant to hydrogen exposure at temperature above 500° C. By tolerant is meant that the catalyst can operate for a much longer period of time without significant loss in activity. In the instant case, the treated catalyst has a lifetime which is at least 6 times longer than a catalyst which has not been treated according to this invention.

The dehydrocyclodimerization conditions which will be employed for use with the catalyst of the present invention will, of course, vary depending on such factors as feedstock composition and desired conversion. A desired range of conditions for the dehydrocyclodimerization of $C_2$–$C_6$ aliphatic hydrocarbons to aromatics include a temperature from about 350° C. to about 650° C., a pressure from about 1 to about 20 atmospheres, and a liquid hourly space velocity from about 0.2 to about 5 $hr^{-1}$. The preferred process conditions are a temperature in the range from about 400° to about 550° C., a pressure in or about the range from 2 to 10 atmospheres and a liquid hourly space velocity of between 0.5 to 2.0 $hr^{-1}$. It is understood that, as the average carbon number of the feed increases, a temperature in the lower end of the temperature range is required for optimum performance and conversely, as the average carbon number of the feed decreases, the higher the required temperature.

The feed stream to the dehydrocyclodimerization process is defined herein as all streams introduced into the dehydrocyclodimerization reaction zone. Included in the feed stream is the $C_2$–$C_6$ aliphatic hydrocarbon. By $C_2$–$C_6$ aliphatic hydrocarbons is meant one or more open, straight or branched chain isomers having from two to six carbon atoms per molecule. Furthermore, the hydrocarbons in the feedstock may be saturated or unsaturated. Preferably, the hydrocarbons $C_3$ and/or $C_4$ are selected from isobutane, normal butane, isobutene, normal butene, propane and propylene. Diluents may also be included in the feed stream. Examples of such diluents include hydrogen, nitrogen, helium, argon, neon.

According to the present invention, the feed stream is contacted with the instant catalyst in a dehydrocyclodimerization reaction zone maintained at dehydrocyclodimerization conditions. This contacting may be accomplished by using the catalyst in a fixed bed system, a moving bed system, a fluidized bed system, or in a batch type operation; however, in view of the danger of attrition losses of the valuable catalyst and of the well-known operational advantages, it is preferred to use either a fixed bed system or a dense-phase moving bed system such as shown in U.S. Pat. No. 3,725,249.

In a fixed bed system or a dense-phase moving bed the feed stream is preheated by any suitable heating means to the desired reaction temperature and then passed into a dehydrocyclodimerization zone containing a bed of the instant catalyst. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion with the latter being preferred. In addition, the reactants are in the vapor phase when they contact the catalyst. The dehydrocyclodimerization system then preferably comprises a dehydrocyclodimerization zone containing one or more fixed or dense-phase moving beds of the instant catalyst. In a multiple bed system, it is, of course, within the scope of the present invention to use the present catalyst in less than all of the beds with another dehydrocyclodimerization or similarly behaving catalyst being used in the remainder of the beds. This dehydrocyclodimerization zone may be one or more separate reactors with suitable heating means therebetween to compensate for any heat loss encountered in each catalyst bed. Specific to the dense-phase moving bed system, it is commmon practice to remove catalyst from the bottom of the reaction zone, regenerate it by conventional means known to the art, and then return it to the top of the reaction zone.

The following examples are presented in illustration of this invention and are not intended as undue limitations on the generally broad scope of the invention as set out in the appended claims.

EXAMPLE 1

This example describes the preparation of a dehydrocyclodimerization catalyst according to the prior art. A first solution was prepared by adding phosphoric acid to an aqueous solution of hexamethylenetatraamine (HMT) in an amount to yield a phosphorus content of the finished catalyst equal to about 11 weight percent. A second solution was prepared by adding a ZSM-5 type zeolite to enough alumina sol, prepared by digesting metallic aluminum in hydrochloric acid, to yield a zeolite content in the finished catalyst equal to about 67 weight percent. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres. These spheres were removed from the oil bath, water washed, air dried, and calcined at a temperature of about 482° C. A solution of gallium nitrate was utilized to impregnate the spheres to achieve a gallium content on the finished catalyst equal to about 1 weight percent. After impregnation, the spheres were dried, then heated in pure hydrogen at 580° C. for 6 hours. The spheres were finally calcined, in the presence of steam, at a temperature of about 649° C. This catalyst was identified as catalyst A.

EXAMPLE 2

This example describes the preparation of a dehydrocyclodimerization catalyst according to the invention. About 100 cc of Catalyst A were added to a round bottom flask equipped with a condenser and containing 500 mL of a 2M ammonium nitrate aqueous solution. This mixture was heated to reflux by means of an oil bath and refluxed for 24 hours. Upon cooling the mixture was filtered and the spheres washed five times with 100 mL of deionized water. The washed spheres were dried at 150° C. for 3 hours and then calcined at 540° C. for 2 hours. This catalyst was identified as catalyst B.

The wash water from the ammonium nitrate treatment was analyzed to determine what elements were present. The analysis of the wash water and catalyst B are presented in Table A.

TABLE A

| Element | Catalyst B (wt. %) | Wash Water (wt. %) |
|---|---|---|
| Si | 23.33 | 0.05 |
| Al | 13.50 | 0.188 |
| P | 10.96 | 0.108 |
| Ga | 1.02 | 0.00003 |

As Table A shows, the species which are removed by the ammonium nitrate wash are composed primarily of aluminum and phosphorus.

EXAMPLE 3

The following test procedure was used to evaluate the dehydrocyclodimerization activity of catalysts. A feedstock of propane was flowed through a reactor containing the catalyst to be tested. The propane was flowed through the reactor at a liquid hourly space velocity of 0.8 hr$^{-1}$ under a pressure of 1 atmosphere and at a reactor inlet temperature of 540° C. The conversion of propane to aromatics was calculated at various times during the testing.

Catalysts A and B were accelerated aged by treating the catalysts with a hydrogen/methane gas feed at 1 atmosphere and 565° C. for a period of 100 hours. The function of the methane is to act as a diluent. After this hydrogen treatment, the catalysts were oxidized in air at 565° C. and then tested as described above. This hydrogen treatment is believed to be analogous to about one month of on stream operation. The results of the testing are presented in Table B.

TABLE B

Effect of NH$_4$NO$_3$ Treatment on the Activity of Aged Catalysts

| Time (Hrs) | Conversion (%) | |
|---|---|---|
| | Catalyst A* (No Treatment) | Catalyst B* (Treated) |
| 11 | 69.9 | 78.3 |
| 23 | 60.4 | 68.8 |
| 35 | 54.8 | 60.1 |
| 47 | N/A | N/A |

*Aged for 100 hours with H$_2$/CH$_4$ at 565° C.

The results presented in Table B show that a catalyst that has been treated with ammonium nitrate has a much higher conversion than one that has not been treated. Therefore, Catalyst B is much more tolerant to hydrogen exposure than Catalyst A.

We claim as our invention:

1. A catalyst for converting C$_2$ to C$_6$ aliphatic hydrocarbons to aromatics comprising a zeolite having a Si:Al ratio greater than about 10 and a pore diameter of about 5-6 Å, a gallium component and an aluminum phosphate binder, the catalyst characterized in that it is tolerant to exposure to hydrogen at a temperature of about 500° to about 700° C.

2. The catalyst of claim 1 where the zeolite is a ZSM family zeolite.

3. The catalyst of claim 1 where the zeolite concentration ranges from about 30 to about 90 weight percent of the catalyst.

4. The catalyst of claim 1 where the gallium content on the catalyst varies from about 0.1 to about 5 weight percent, as the metal, of the catalyst.

5. A process for preparing a catalyst for converting C$_2$ to C$_6$ aliphatic hydrocarbons to aromatics comprising: a) forming particles from a mixture of a zeolite and an aluminum phosphate binder; b) calcining said particles at a temperature of about 500° to about 700° C. and for a time of about 1 to about 15 hours; c) impregnating the calcined particles with a gallium salt; d) heating the gallium containing particles in hydrogen at a temperature of about 500° to about 700° C. for a time of about 1 to about 15 hours, followed by heating in an air/steam mixture at a temperature of about 400° to about 700° C. for a time of about 1 to about 10 hours; e) treating the particles of step (d) with an aqueous solution of a weakly acidic ammonium salt or a dilute acid solution at a temperature of about 50° to about 100° C. for a time of about 1 to about 48 hours; and f) calcining the particles at a temperature of about 500° to about 700° C. for a time of about 1 to about 15 hours, thereby providing said catalyst.

6. The process of claim 5 where the gallium content on the catalyst varies from about 0.1 to about 5 weight percent, as the metal, of the catalyst.

7. The process of claim 5 where the zeolite concentration varies from about 30 to about 90 weight percent of the catalyst.

8. The process of claim 7 where the zeolite concentration varies from about 50 to about 70 weight percent of the catalyst.

9. The process of claim 5 where the zeolite is a ZSM family zeolite.

* * * * *